(12) United States Patent
Preuss et al.

(10) Patent No.: US 8,888,861 B2
(45) Date of Patent: Nov. 18, 2014

(54) ASYMMETRIC DESIGN OF HIP SOCKET FOR REDUCING SOCKET DEFORMATIONS

(75) Inventors: Roman Preuss, Leinf.-Echterdingen (DE); Thomas Pandorf, Esslingen-Zell (DE)

(73) Assignee: CeramTec GmbH, Plochingen (DE)

( * ) Notice: Subject to any disclaimer, the term of this patent is extended or adjusted under 35 U.S.C. 154(b) by 186 days.

(21) Appl. No.: 12/375,715

(22) PCT Filed: Aug. 6, 2007

(86) PCT No.: PCT/EP2007/058127
§ 371 (c)(1),
(2), (4) Date: Jan. 30, 2009

(87) PCT Pub. No.: WO2008/015289
PCT Pub. Date: Feb. 7, 2008

(65) Prior Publication Data
US 2009/0287311 A1    Nov. 19, 2009

(30) Foreign Application Priority Data

Aug. 4, 2006  (DE) .......................... 10 2006 036 924
Jul. 6, 2007   (DE) .......................... 10 2007 031 669

(51) Int. Cl.
*A61F 2/32*   (2006.01)
*A61F 2/34*   (2006.01)
*A61F 2/36*   (2006.01)
*A61F 2/30*   (2006.01)

(52) U.S. Cl.
CPC ........... *A61F 2/34* (2013.01); *A61F 2250/0018* (2013.01); *A61F 2/32* (2013.01); *A61F 2/3662* (2013.01); *A61F 2002/30324* (2013.01); *A61F 2310/00011* (2013.01); *A61F 2002/3611* (2013.01); *A61F 2002/3469* (2013.01); *A61F 2250/0036* (2013.01); *A61F 2002/365* (2013.01); *A61F 2/36* (2013.01); *A61F 2002/30733* (2013.01); *A61F 2002/30014* (2013.01); *A61F 2002/3496* (2013.01); *A61F 2002/3454* (2013.01); *A61F 2002/3625* (2013.01)
USPC ....................................... 623/22.24

(58) Field of Classification Search
CPC ............ A61F 2/34; A61F 2002/30014; A61F 2002/30018
USPC ...................... 623/22.21–22.28, 22.29–22.39, 623/22.4–22.46
See application file for complete search history.

(56) References Cited

U.S. PATENT DOCUMENTS 2,910,978 A * 11/1959 Urist .......................... 623/22.21
3,840,904 A * 10/1974 Tronzo ....................... 623/22.32

(Continued)

FOREIGN PATENT DOCUMENTS

DE    44 42 559 A1    6/1995
DE    197 01 778 A1   6/1998

(Continued)

*Primary Examiner* — Alvin Stewart
(74) *Attorney, Agent, or Firm* — Fulbright & Jaworski LLP

(57) ABSTRACT

A hip socket for use in a hip joint prosthesis comprising a shaft on which a ball head may be fixed, the ball head may be rotatably inserted in a socket insert and the socket insert may be inserted and fixed in the hip socket the shaft and the hip socket being implantable in the thigh bone and the pelvic bone respectively. Damages to the socket insert and/or limitation of the function of the sliding pair of ball head/socket insert may be avoided by local reduction of the calotte diameter of the socket insert, such that the hip socket has an asymmetrical design with regard to the stiffness and/or geometry thereof in two different directions (x, y) orthogonal to each other and to the symmetry axis (z) of the hip socket.

5 Claims, 3 Drawing Sheets

(56) References Cited

U.S. PATENT DOCUMENTS

Figure 3A:
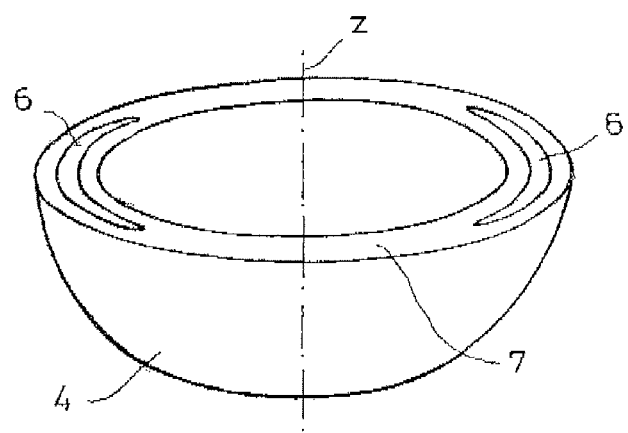

| | | | |
|---|---|---|---|
| 3,903,549 A * | 9/1975 | Deyerle | 623/22.36 |
| 4,159,544 A * | 7/1979 | Termanini | 623/22.14 |
| 4,324,006 A * | 4/1982 | Charnley | 623/22.21 |
| 4,619,658 A * | 10/1986 | Pappas et al. | 623/22.19 |
| 4,623,352 A * | 11/1986 | Oh | 623/22.28 |
| 4,650,491 A * | 3/1987 | Parchinski | 623/22.28 |
| 4,718,911 A * | 1/1988 | Kenna | 623/22.29 |
| 4,778,474 A * | 10/1988 | Homsy | 623/22.14 |
| 4,828,565 A * | 5/1989 | Duthoit et al. | 623/22.3 |
| 4,834,759 A * | 5/1989 | Spotorno et al. | 623/22.3 |
| 4,840,631 A * | 6/1989 | Mathys | 623/22.14 |
| 5,108,448 A * | 4/1992 | Gautier | 623/22.26 |
| 5,133,764 A * | 7/1992 | Pappas et al. | 623/23.14 |
| 5,171,286 A | 12/1992 | Lawes et al. | |
| 5,192,329 A * | 3/1993 | Christie et al. | 623/22.22 |
| 5,226,917 A * | 7/1993 | Schryver | 623/22.37 |
| 5,326,368 A * | 7/1994 | Collazo | 623/22.22 |
| 5,370,703 A * | 12/1994 | Willert et al. | 623/22.22 |
| 5,370,704 A * | 12/1994 | DeCarlo, Jr. | 623/22.22 |
| 5,376,122 A * | 12/1994 | Pappas et al. | 623/22.28 |
| 5,507,824 A * | 4/1996 | Lennox | 623/22.25 |
| 5,507,828 A | 4/1996 | Maumy et al. | |
| 5,725,591 A * | 3/1998 | DeCarlo et al. | 623/22.29 |
| 5,824,107 A * | 10/1998 | Tschirren | 623/22.28 |
| 5,879,398 A * | 3/1999 | Swarts et al. | 623/22.21 |
| 5,928,288 A * | 7/1999 | Wilson | 623/22.22 |
| 5,938,702 A * | 8/1999 | Lopez et al. | 623/22.38 |
| 5,976,148 A * | 11/1999 | Charpenet et al. | 606/91 |
| 6,059,833 A * | 5/2000 | Doets | 623/22.21 |
| 6,136,033 A * | 10/2000 | Suemer | 623/22.21 |
| 6,187,050 B1 * | 2/2001 | Khalili et al. | 623/22.22 |
| 6,290,727 B1 * | 9/2001 | Otto et al. | 623/22.21 |
| 6,293,971 B1 * | 9/2001 | Nelson et al. | 623/23.63 |
| 6,312,473 B1 * | 11/2001 | Oshida | 623/23.55 |
| 6,319,285 B1 * | 11/2001 | Chamier et al. | 623/22.32 |
| 6,325,829 B1 * | 12/2001 | Schmotzer | 623/22.21 |
| 6,454,809 B1 * | 9/2002 | Tornier | 623/22.32 |
| 6,475,243 B1 * | 11/2002 | Sheldon et al. | 623/22.28 |
| 6,488,715 B1 * | 12/2002 | Pope et al. | 623/22.21 |
| 6,517,583 B1 * | 2/2003 | Pope et al. | 623/23.6 |
| 6,537,321 B1 * | 3/2003 | Horber | 623/22.22 |
| 6,558,428 B2 | 5/2003 | Park | 623/23.59 |
| 6,589,284 B1 * | 7/2003 | Silberer | 623/22.29 |
| 6,641,617 B1 * | 11/2003 | Merrill et al. | 623/23.58 |
| 6,682,566 B2 * | 1/2004 | Draenert | 623/22.24 |
| 6,811,569 B1 * | 11/2004 | Afriat et al. | 623/22.32 |
| 6,896,703 B2 * | 5/2005 | Barbieri et al. | 623/22.3 |
| 6,942,701 B2 * | 9/2005 | Taylor | 623/22.14 |
| 6,966,932 B1 * | 11/2005 | Schroeder | 623/22.19 |
| 7,074,241 B2 * | 7/2006 | McKinnon | 623/22.24 |
| 7,090,678 B2 * | 8/2006 | Cotting et al. | 606/81 |
| 7,169,185 B2 * | 1/2007 | Sidebotham | 623/22.21 |
| 7,241,315 B2 * | 7/2007 | Evans | 623/23.12 |
| 7,335,231 B2 * | 2/2008 | McLean | 623/22.15 |
| 7,553,332 B2 * | 6/2009 | Bacon | 623/22.3 |
| 7,572,295 B2 * | 8/2009 | Steinberg | 623/22.23 |
| 7,578,851 B2 * | 8/2009 | Dong et al. | 623/22.21 |
| 7,682,398 B2 * | 3/2010 | Croxton et al. | 623/22.24 |
| 7,695,521 B2 * | 4/2010 | Ely et al. | 623/22.21 |
| 7,776,097 B2 * | 8/2010 | Tepic et al. | 623/22.24 |
| 7,780,740 B2 * | 8/2010 | Steinberg | 623/22.21 |
| 7,794,504 B2 * | 9/2010 | Case | 623/22.21 |
| 7,819,925 B2 * | 10/2010 | King et al. | 623/23.58 |
| 7,896,921 B2 * | 3/2011 | Smith et al. | 623/19.11 |
| 7,938,861 B2 * | 5/2011 | King et al. | 623/18.11 |
| 8,021,432 B2 * | 9/2011 | Meridew et al. | 623/22.32 |
| 8,197,550 B2 * | 6/2012 | Brown et al. | 623/22.32 |
| 8,211,184 B2 * | 7/2012 | Ries et al. | 623/22.21 |
| 8,226,728 B2 * | 7/2012 | Preuss et al. | 623/22.14 |
| 8,574,306 B2 * | 11/2013 | Ries et al. | 623/22.21 |
| 2001/0011190 A1 * | 8/2001 | Park | 623/11.11 |
| 2005/0060040 A1 * | 3/2005 | Auxepaules et al. | 623/22.18 |
| 2005/0071015 A1 * | 3/2005 | Sekel | 623/22.28 |
| 2005/0143836 A1 * | 6/2005 | Steinberg | 623/22.23 |
| 2006/0178497 A1 * | 8/2006 | Gevaert et al. | 528/44 |
| 2007/0150068 A1 * | 6/2007 | Dong et al. | 623/22.32 |
| 2007/0173948 A1 * | 7/2007 | Meridew et al. | 623/22.24 |
| 2007/0191962 A1 * | 8/2007 | Jones et al. | 623/22.32 |
| 2007/0219640 A1 * | 9/2007 | Steinberg | 623/22.12 |
| 2008/0208353 A1 * | 8/2008 | Kumar et al. | 623/23.56 |
| 2008/0255674 A1 * | 10/2008 | Rahaman et al. | 623/23.11 |
| 2009/0018666 A1 * | 1/2009 | Grundei et al. | 623/22.21 |
| 2009/0088865 A1 * | 4/2009 | Brehm | 623/22.21 |
| 2009/0088866 A1 * | 4/2009 | Case | 623/22.21 |
| 2009/0177282 A1 * | 7/2009 | Bureau et al. | 623/16.11 |
| 2009/0326670 A1 * | 12/2009 | Keefer et al. | 623/22.22 |
| 2010/0063596 A1 * | 3/2010 | Imhof | 623/22.22 |
| 2010/0179663 A1 * | 7/2010 | Steinberg | 623/22.24 |
| 2011/0015752 A1 * | 1/2011 | Meridew | 623/22.24 |
| 2011/0151027 A1 * | 6/2011 | Clineff et al. | 424/722 |
| 2011/0151259 A1 * | 6/2011 | Jarman-Smith et al. | 428/402 |
| 2011/0153025 A1 * | 6/2011 | McMinn | 623/20.32 |
| 2011/0190901 A1 * | 8/2011 | Weissberg et al. | 623/22.24 |
| 2013/0268084 A1 * | 10/2013 | McMinn | 623/22.32 |

FOREIGN PATENT DOCUMENTS

| | | |
|---|---|---|
| DE | 203 00 018 U1 | 3/2003 |
| EP | 0 380 045 A | 8/1990 |
| EP | 0 472 318 A | 2/1992 |
| EP | 0 640 324 A | 3/1995 |

* cited by examiner

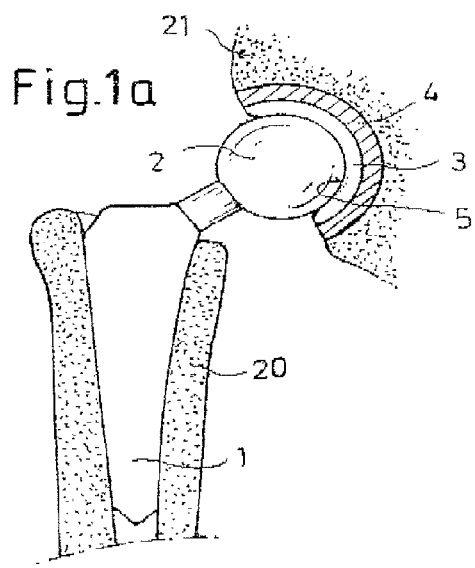
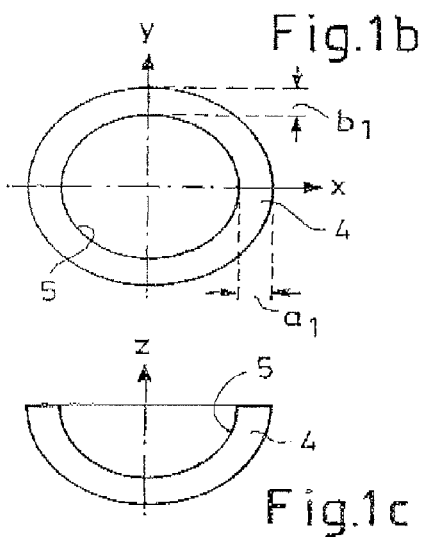
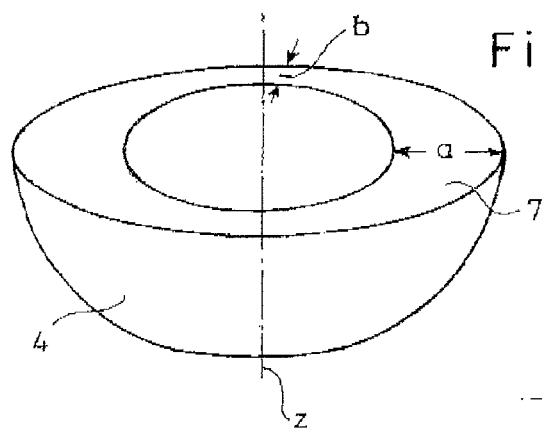

ASYMMETRIC DESIGN OF HIP SOCKET FOR REDUCING SOCKET DEFORMATIONS

This application is a §371 of PCT/EP2007/058127 filed Aug. 6, 2007, which claims priority from DE 10 2006 036 924.6 filed Aug. 4, 2006 and DE 10 2007 031 669.2 filed Jul. 6, 2007.

The invention relates to a hip socket for use for a hip-joint prosthesis that consists of a shaft on which a ball head can be fastened, which ball head can be inserted into a socket insert in a rotatable manner, and the socket insert can be inserted and fixed in the hip socket, wherein the shaft can be implanted into the femur, and the hip socket can be implanted into the pelvic bone.

Hip sockets are coupled with the pelvic bone by means of various techniques during the course of the operation for the purposes of primary fixation. A common way of fixing is to clamp the socket by means of a press fit. This represents a form of coupling which in the technical sense can be classed with interference connections. This means that the outer geometry of the hip socket is greater than the socket receiver that has been created by the doctor by milling out the acetabulum. The normal forces that act on the socket through the bone after the introduction of the socket and consequently friction forces guarantee the primary anchorage of the hip socket.

On account of the inhomogeneous rigidity of the pelvic bone, as a rule asymmetrical loading of the hip socket ensues in the press-fit situation, the consequence of which can be asymmetrical deformation of the hip socket. This is basically undesirable, since the deformation of the hip socket makes the introduction of the socket inserts difficult and, furthermore, can lead to the loading and asymmetrical deformation of the socket inserts. Possible further effects are then damage to the socket insert and/or limitation of the function of the sliding pairing as a result of a local reduction in the hemispherical-recess diameter of the socket insert.

The inhomogeneity of the pelvic bone with regard to rigidity as a rule is always in the same direction so the doctor can estimate the direction of the greatest load for the hip socket in the press fit with sufficient accuracy with respect to the patient.

The underlying object of the invention is to develop further a hip socket in accordance with the preamble of claim 1 in such a way that damage to the socket insert and/or a limitation of the function of the sliding pairing ball-head/socket-insert as a result of a local reduction in the hemispherical-recess diameter of the socket insert are/is avoided.

In accordance with the invention, this object is achieved in that the hip socket is formed asymmetrically with regard to its rigidity and/or geometry in two directions that are orthogonal to each other and to the axis of symmetry of the hip socket. As a result of this specific asymmetrical design of the hip socket with regard to its rigidity and/or geometry, it is possible to counteract the asymmetrical outer loading in the press-fit situation. The hip socket thus has different rigidities in two orthogonal directions.

The axis of higher rigidity of the hip socket can be aligned during the implantation so as to be collinear with respect to the direction of the greatest rigidity of the pelvic bone. The result of corresponding dimensioning of the rigidities of the hip socket in relation to the rigidities of the pelvic bone can be that the unavoidable deformation of the hip socket as a result of the press-fit situation occurs uniformly, that is, with deformation paths that are almost identical in terms of amount over the whole socket periphery.

In an inventive development, the hip socket has in a first direction a minimum wall thickness and in a second direction a maximum wall thickness. This asymmetrical design of the wall thickness of the hip socket is achieved, for example, in such a way that in the region of the end face in one direction a minimum wall thickness is realized and orthogonally thereto a maximum wall thickness is realized. On account of the differing wall thicknesses, the hip socket likewise has differing rigidity in the two directions mentioned.

In a further development, stiffening or weakening elements are introduced into the hip socket in one direction in relation to the other direction. By introducing stiffening elements—elements made from a material with a higher level of rigidity—into the casing of the hip socket, likewise differing rigidities of the hip socket can be achieved in various loading directions.

A development of the invention is characterised in that the stiffening or weakening elements of one direction constantly reduce or increase the rigidity thereof towards the other direction. The weakening elements can also be recesses in the hip socket.

By introducing elements made from a material with a lower level of rigidity, the rigidity of the hip socket is weakened at the site of the material with a lower level of rigidity, with the measure of the decrease in rigidity being directionally dependent. The hip socket consequently has with regard to different loading directions likewise different levels of rigidity. In the extreme case, no elements are introduced, but material is just recessed in a corresponding manner in order to reduce the rigidity in a directionally dependent manner.

In a further embodiment, the geometry of the hip socket is formed asymmetrically in such a way that in the case of asymmetrical loading a symmetrical geometry that is as circular-ring-shaped as possible results. Advantageously, the cross-section of the hip socket is oval perpendicularly to the axis of symmetry in the unloaded state.

By means of an asymmetrical design of the socket geometry, for example of the loaded socket cross-section, it is possible to achieve a situation where, when there is asymmetrical loading, a likewise asymmetrical deformation occurs that leads to the formation of a symmetrical socket geometry. In the concrete example, an oval socket cross-section is deformed in consequence of the asymmetrical loading in the press fit until the cross-section has an almost circular-ring-shaped geometry.

The hip socket is preferably made from at least one metal.

The prior art and the invention are explained in greater detail in the following with the aid of figures.

FIGS. 1*a*, 1*b*, 1*c* show the prior art. A hip-joint prosthesis as a rule consists of a shaft 1 coupled with a ball head 2 and of a hip socket 4 coupled with a socket insert 3. The shaft 1 and the hip socket 4 are connected to the body of the patient as a result of growing into the femur 20 and the pelvic bone 21 respectively and are carriers for the ball head 2 and the socket insert 3 respectively. The ball head 2 is rotatably mounted in the hemispherical recess 5 of the socket insert 3. The hip socket 4 is formed in a rotationally symmetrical manner with regard to its axis of symmetry z, whereby the wall thicknesses $a_1$, $b_2$ of the hip socket 4 are identical in all directions x, y, and the consequence of asymmetrical loading of the hip socket 4 in the press-fit situation can be asymmetrical deformation of the hip socket 4.

FIG. 2 *a, b* shows a hip socket 4 in accordance with the invention that is set up so that it is not symmetrical in the plane of the end face 7 (see FIG. 2 *a*). The wall thickness a in a direction that is orthogonal to the axis of symmetry z is the maximum and the wall thickness b likewise in a direction y that is likewise orthogonal to the axis of symmetry z is the minimum. The directions x, y are then arranged orthogonally, that is, at right angles to each other.

On account of the different wall thicknesses a, b, the hip socket 4 has different rigidities in the two directions x, y mentioned.

Figure 3B:
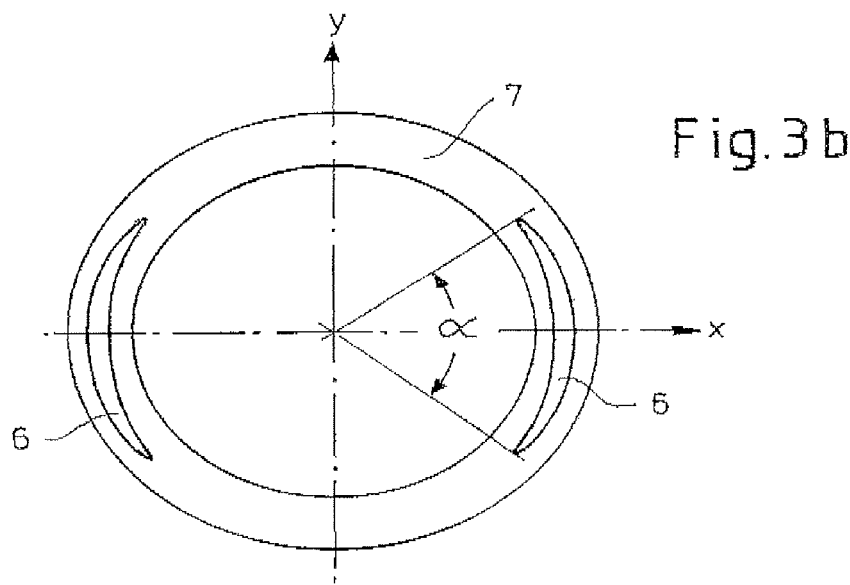

FIG. 3 shows a hip socket 4 in accordance with the invention in which elements 6 that act in a stiffening or weakening manner in one direction x with regard to the other orthogonal direction y are introduced into the hip socket. As a result of introducing these stiffening or weakening elements 6—elements made from a material with a higher or lower level of rigidity than the rest of the material of the hip socket 4—into the casing of the hip socket 4, different levels of rigidity of the hip socket 4 are realized with regard to various loading directions.

The stiffening or weakening elements 6 of one direction x then cover an angular range a on the end face of approximately 90 degrees (see FIG. 3 b). What is important is that the rigidity in one direction x differs from the rigidity in a direction y orthogonal to the direction x. In order to achieve a homogeneous change in rigidity between the two extreme values with regard to the direction x and y, the stiffening or weakening elements can cover an angle α of up to 180°, with the wall thickness of the respective element increasing continuously from one end as far as the centre of the element and decreasing again just as continuously towards the other end.

As a result of introducing elements 6 consisting of a material with, for example, a lower level of rigidity, the rigidity of the hip socket 4 is weakened at the site of the material with a lower level of rigidity, with the measure of the decrease in rigidity being directionally dependent. The hip socket 4 consequently has in the case of different loading directions likewise different levels of rigidity. In the extreme case, no elements are introduced, but material is just recessed out in a corresponding manner in order to reduce the rigidity in a directionally dependent manner.

Figure 4A:
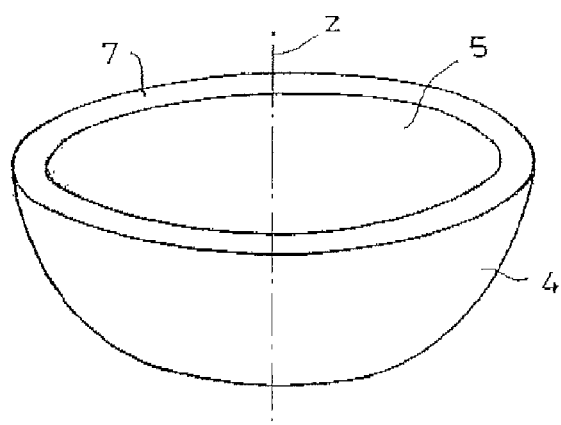
Figure 4B:
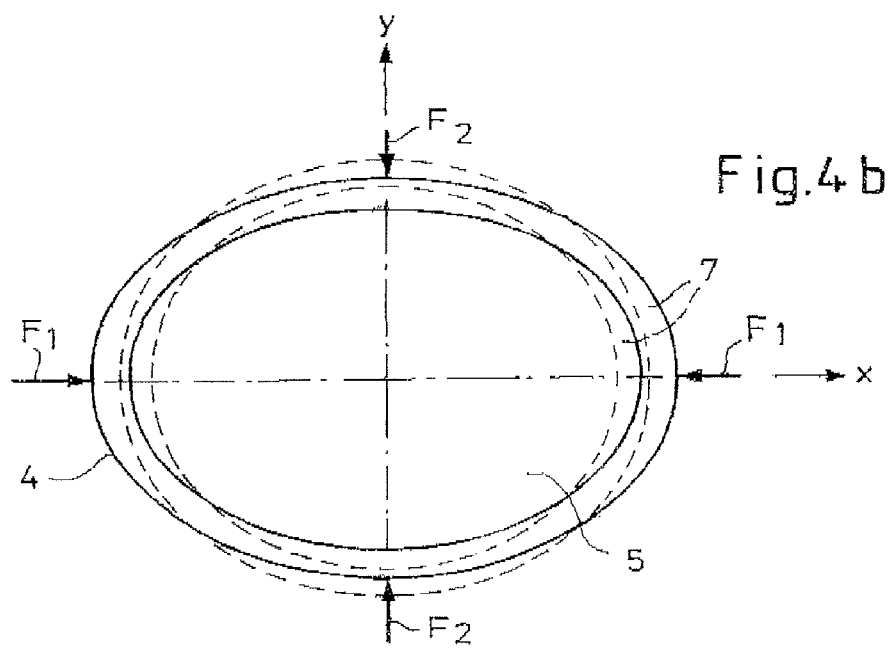

FIG. 4 b shows a hip socket 4 whose geometry is formed asymmetrically in such a way that the cross-section of the hip socket 4 is oval perpendicularly with respect to the axis of symmetry z in the unloaded state (continuous line). In the event of asymmetrical loading, the hip socket 4 is deformed (see broken line in FIG. 4 b) so that as a result a symmetrical geometry occurs. FIG. 4 a shows the hip socket 4 in the loaded state. The forces that occur at points in the simplified model presentation are marked with $F_1$, $F_2$. In the case of this embodiment, it is to be ensured that given asymmetrical loading (in direction $F_1$), a symmetrical geometry that is as circular-ring-shaped as possible results (see FIG. 4a).

As a result of this asymmetrical design of the geometry of the hip socket 4, with asymmetrical loading a likewise asymmetrical deformation can occur that can lead to the formation of a symmetrical socket geometry. In the concrete example, an oval socket cross-section is deformed in consequence of the asymmetrical loading in the press fit until the cross-section has an almost circular-ring-shaped geometry.

The invention claimed is:

1. A hip socket for a hip-joint prosthesis comprising: stiffening elements; wherein the hip socket has a dome shaped structure, an axis of symmetry extending along a length of the hip socket and an end face, the end face extending along a transverse plane that is orthogonal to the axis of symmetry of the hip socket; wherein the hip socket is asymmetrically structured so that the hip socket has at least one of a different rigidity in first and second directions, wherein the first and the second directions are orthogonal to each other and to the axis of symmetry of the hip socket, wherein the first and second directions extend along the transverse plane, wherein the axis of symmetry is coaxial with a central axis of the hip socket, wherein the stiffening elements are located in the hip socket in the first direction in relation to the second direction, and the stiffening elements are made from a material with a higher level of rigidity than the rest of the material of the hip socket, wherein a press-fit force to the hip socket causes deformation of the hip socket.

2. A hip socket according to claim 1, wherein the stiffening elements of the first direction increase the rigidity along the first direction relative to the second direction.

3. A hip socket according to claim 2, wherein the hip socket is made from at least one metal.

4. A hip socket according to claim 1, wherein the hip socket is made from at least one metal.

5. A hip socket comprising: an end face; wherein the hip socket has an asymmetrical geometry; wherein a cross-section of the hip socket is oval perpendicularly with respect to a central axis of symmetry in the unloaded state and wherein upon asymmetrical loading, the hip socket is deformed so that a symmetrical geometry of the hip socket occurs in a loaded state.

* * * * *